United States Patent [19]

Harada et al.

[11] Patent Number: 5,973,184
[45] Date of Patent: Oct. 26, 1999

[54] PROCESS FOR PREPARING A DIALKYL CARBONATE BY GAS-PHASE DECARBONYLATION OF DIALKYL OXALATE

[75] Inventors: Katsumasa Harada; Ryoji Sugise; Masayuki Nishio; Toshio Kurafuji; Toshihiro Shimakawa, all of Yamaguchi, Japan

[73] Assignee: Ube Industries, Ltd., Yamaguchi, Japan

[21] Appl. No.: 09/188,829

[22] Filed: Nov. 9, 1998

[30] Foreign Application Priority Data

Nov. 7, 1997 [JP] Japan .................................... 9-305183

[51] Int. Cl.[6] .................................................... C07C 68/00
[52] U.S. Cl. ............................................................ 558/277
[58] Field of Search ................................................ 558/277

[56] References Cited

U.S. PATENT DOCUMENTS 4,544,507 10/1985 Foley ........................................ 558/274
5,648,510 7/1997 Harada et al. ........................... 558/274

*Primary Examiner*—Michael G. Ambrose
*Attorney, Agent, or Firm*—McAulay Nissen Goldberg Kiel & Hand, LLP

[57] ABSTRACT

A dialkyl carbonate (e.g., dimethyl carbonate) is prepared at a high yield and a high selectivity by decarbonylation of a dialkyl oxalate (e.g., dimethyl oxalate) in a gaseous phase in the presence of an alkali metal compound (e.g., potassium carbonate).

13 Claims, No Drawings

PROCESS FOR PREPARING A DIALKYL CARBONATE BY GAS-PHASE DECARBONYLATION OF DIALKYL OXALATE

FIELD OF THE INVENTION

The present invention relates to a process for prearing a dialkyl carbonate. In more detail, the invention relates to an improvement in the preparation of a dialkyl carbonate from a dialkyl oxalate.

BACKGROUND OF THE INVENTION

The dialkyl carbonate is utilized in industry to prepare pharmaceutically active compounds, agricultural chemicals, urethane, and polycarbonate or is as such utilized as a solvent.

U.S. Pat. No. 4,544,507 discloses that the dialkyl carbonate can be prepared by heating a dialkyl oxalate in a liquid phase at a temperature of 50 to 150° C. in the presence of an alcoholate catalyst, by which the dialkyl oxalate is decarbonylated. This preparation process in the liquid phase has disadvantageous features in that separation and recovery of the produced dialkyl carbonate and the catalyst from the reaction mixture require complicated procedures. Moreover, this process is not satisfactory from the viewpoint of industrial production, because the yield of the target dialkyl carbonate is low and further the selectivity to the target dialkyl carbonate is low due to accompanying side-reactions which give various by-products.

SUMMARY OF THE INVENTION

It is an object of the invention to provide an improved process of the preparation of a dialkyl carbonate by decarbonylation of a dialkyl oxalate which enables production of the dialkyl carbonate in a high yield, specifically a high space time yield, and a high selecivity with no necessity of complicated procedures for separation and recovery.

The present invention resides in a process for preparing a dialkyl carbonate which comprises decarbonylation of a dialkyl oxalate in a gaseous phase in the presence of an alkali metal compound.

DETAILED DESCRIPTION OF THE INVENTION

The process for preparing a dialkyl carbonate from a dialkyl oxalate can be illustrated as follows:

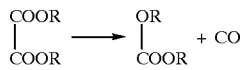

wherein R stands for an unsubstituted or substituted alkyl group.

In these formulas, R is an alkyl group having 1 to 20, preferably 1 to 4, carbon atoms, such as methyl, ethyl, n-propyl, isopropyl, n-butyl, isobutyl and tert-butyl. Two R in one formula can be the same or different from each other. Examples of dialkyl oxalates include dimethyl oxalate, diethyl oxalate, and methyl ethyl oxalate.

The decarbonylation reaction according to the invention is performed in a gaseous phase in the presence of an alkali metal compound catalyst. The alkali metal compound can be an organic acid salt of an alkali metal, an inorganic acid salt of an alkali metal, a hydroxide of an alkali metal, or an oxide of alkali metal. Two or more alkali metal compounds can be employed in combination.

The organic acid salt of an alkali metal can be an alkali metal aliphatic monocarboxylate having 1 to 10 carbon atoms such as sodium acetate, potassium acetate, rubidium acetate, cesium acetate, sodium propionate, potassium propionate, rubidium propionate, cesium propionate, sodium butanoate, potassium butanoate, rubidium butanoate, cesium butanoate, sodium methyl oxalate, potassium methyl oxalate, rubidium methyl oxalate, or cesium methyl oxalate; an alkali metal aliphatic dicarboxylate having 2 to 10 carbon atoms such as sodium oxalate, potassium oxalate, rubidium oxalate, cesium oxalate, sodium adipate, potassium adipate, rubidium adipate, or cesium adipate; or an alkali metal aromatic carboxylate having 7 to 12 carbon atoms such as sodium benzoate, potassium benzoate, rubidium benzoate, or cesium benzoate.

The inorganic acid salt of an alkali metal can be an alkali metal carbonate such as sodium carbonate, potassium carbonate, sodium potassium carbonate, rubidium carbonate, cesium carbonate, sodium methyl carbonate, potassium methyl carbonate, rubidium methyl carbonate, or cesium methyl carbonate; an alkali metal halide such as potassium chloride, rubidium chloride, cesium chloride, potassium bromide, rubidium bromide, or cesium bromide; an alkali metal nitrate such as potassium nitrate, rubidium nitrate, or cesium nitrate; an alkali metal phosphate such as potassium phosphate, rubidium phosphate, or cesium phosphate.

The hydroxide of an alkali metal can be potassium hydroxide, rubidium hydroxide, or cesium hydroxide.

The oxide of an alkali metal can be potassium oxide, rubidium oxide, or cesium oxide.

Preferred are an inorganic acid salt of an alkali metal and an organic acid salt of an alkali metal. Particularly preferred are an alkali metal carbonate, an alkali metal aliphatic monocarboxylate, and an alkali metal aliphatic dicarboxylate such as an alkali metal oxalate.

The alkali metal compound, which serves as a catalyst, can be utilized per se in the form of a powder, granules, pulverized pieces, beads, or a molded article. If necessary, the alkali metal compound can be deposited on a carrier such as an active carbon, silica, alumina (α-alumina or γ-alumina), silica alumina, spinel, spinel-like material, silicon carbide, titania, magnesia, zirconia, or molecular sieves. The alkali metal compound can be deposited on a carrier by a known method such as impregnation, mixing, or kneading. The carrier on which the alkali metal compound is deposited is preferably dried to 100–700° C. under an atmospheric condition or in a stream of a nitrogen gas. The alkali metal compound is preferably deposited on a carrier in an amount of 0.01 to 80 weight %, more preferably in an amount of 0.1 to 50 weight %, in terms of the amount of alkali metal.

The carrier can be utilized in the form of a powder, granules, pulverized pieces, beads or a molded article. The powder can be a mass of fine particles having a diameter in the range of 20 to 100 μm. The granules, pulverized pieces, and beads can have a size of 4 to 200 meshes. The molded article can have a length of 0.5 to 10 mm. The carrier preferably has a specific surface area in the range of 0.1 to 3,000 m²/g, more preferably 10 to 3,000 m²/g, which is measured by the known BET method.

The decarbonylation reaction of a dialkyl oxalate according to the invention is performed in a gaseous phase by heating the dialkyl oxalate in the presence of the alkali metal compound (i.e., catalyst) which is preferably deposited on a carrier. Under the conditions, the dialkyl oxalate is converted into a dialkyl carbonate, according to the aforementioned reaction equation. In the reaction, carbon monoxide is produced. The catalyst can be utilized on a fixed bed or on a fluid bed. Generally, the fixed bed is employed. The reaction vessel preferably is a reaction pipe of stainless steel or quartz.

In industry, the decarbonylation reaction of the invention is preferably performed according to a continuous reaction system. In the continuous reaction system, a gaseous mixture containing a dialkyl oxalate is passed into a reaction vessel charged with the catalyst, preferably, at a space velocity in the range of 100 to 5,000 $h^{-1}$, more preferably 400 to 3,000 $h^{-1}$. The gaseous mixture can comprise the dialkyl oxalate, an organic solvent (e.g., an alcohol or an aromatic hydrocarbon such as toluene), and an inert gas (e.g., nitrogen gas). The reaction temperature is preferably adjusted to 170–450° C., more preferably 200–400° C., most preferably 200–300° C. The reaction can be performed under an atmospheric pressure, an elevated pressure, or a reduced pressure.

The gaseous mixture containing a dialkyl oxalate can be produced by vaporizing a solution of a dialkyl oxalate in an organic solvent (e.g., alcohol), optionally in a stream of an inert gas (e.g., nitrogen gas) in a vaporizer or a reaction vessel. The dialkyl oxalate solution preferably has a dialkyl oxalate concentration of 10 wt. % or more. A dialkyl oxalate alone can be vaporized in the vaporizer or a reaction vessel, if desired.

After the reaction is complete, the produced dialkyl carbonate is separated and recovered by taking a gaseous reaction mixture out of the reaction vessel, condensing it, and subjecting it to distillation.

The present invention is further described by the following examples.

In the examples, the "conversion ratio of dialkyl oxalate", "selectivity to dialkyl carbonate", and "STY (space time yield) of dialkyl carbonate) are defined by the following equations.

Conversion ratio of dialkyl oxalate (%)=100×[amount of consumed dialkyl oxalate (mmol/h)]/[amount of supplied dialkyl oxalate (mmol/h)]

Selectivity to dialkyl carbonate (%)=100×[amount of produced dialkyl carbonate (mmol/h)]/[amount of consumed dialkyl oxalate (mmol/h)]

Space time yield (STY) of dialkyl carbonate (g/L·h)=100×[amount of produced dialkyl carbonate (g)]/[amount of catalyst (L)× reaction time (h)]

EXAMPLE 1

Preparation of Catalyst/carrier Composition

To an aqueous solution of potassium carbonate (1 g) in water (50 mL) was added 10 g of active carbon having a specific surface area of 1,000 $m^2$/g. The mixture was placed under a reduced pressure of 30 mmHg and heated from room temperature to 80° C. for gradually evaporating water. Thereafter, the residue was dried in a nitrogen gas at 200° C. for one hour. The potassium carbonate was deposited on the active carbon (carrier) at a ratio of 5.7 weight % in terms of the amount of potassium.

Preparation of Dimethyl Carbonate

In a quartz reaction tube (inner diameter: 18 mm, length: 400 mm) was charged 5 mL of the catalyst/carrier composition obtained above to form a catalyst layer. The catalyst was heated and maintained at 205° C. From the top of the reaction tube, fused dimethyl oxalate was introduced at a rate of 66.7 mmol/h. The introduced dimethyl oxalate was evaporated before it arrived at the catalyst layer. Then, the evaporated dimethyl oxalate was reacted on the catalyst at 205° C. under an atmospheric pressure. After the reaction was carried out for two hours, the gaseous reaction mixture was caught in an ice-chilled trap. The obtained liquid reaction mixture was analyzed by gas chromatography. The analysis indicated that a conversion ratio of dimethyl oxalate was 100%, a selectivity to dimethyl carbonate was 95.0%, and a space time yield (STY) of dimethyl carbonate was 1,142 g/L·h.

EXAMPLE 2

Preparation of Catalyst/carrier Composition

The procedures of Example 1 were repeated except for replacing 1 g of potassium carbonate with 1 g of sodium carbonate, to give a catalyst deposited on an active carbon. The sodium carbonate was deposited on the active carbon at a ratio of 4.3 weight % in terms of the amount of sodium.

Preparation of Dimethyl Carbonate

In a quartz reaction tube having the same size as that of Example 1 was charged 5 mL of the catalyst/carrier composition obtained above to form a catalyst layer. The catalyst was heated and maintained at 250° C. From the top of the reaction tube, fused dimethyl oxalate was introduced at a rate of 55.6 mmol/h. The introduced dimethyl oxalate was evaporated before it arrived at the catalyst layer. Then, the evaporated dimethyl oxalate was reacted on the catalyst at 250° C. under an atmospheric pressure. After the reaction was carried out for four hours, the gaseous reaction mixture was caught in an ice-chilled trap. The obtained liquid reaction mixture was analyzed by gas chromatography. The analysis indicated that a conversion ratio of dimethyl oxalate was 87.2%, a selectivity to dimethyl carbonate was 75.1%, and a space time yield (STY) of dimethyl carbonate was 656 g/L·h.

EXAMPLE 3

Preparation of Catalyst/carrier Composition

The procedures of Example 1 were repeated except for replacing 1 g of potassium carbonate with 1 g of sodium-potassium carbonate, to give a catalyst deposited on an active carbon. The sodium-potassium carbonate was deposited on the active carbon at a ratio of 5.1 weight % in terms of the amounts of sodium and potassium.

Preparation of Dimethyl Carbonate

The procedures of Example 1 were repeated using 5 mL of the above-prepared catalyst/carrier composition except that the reaction temperature was changed to 230° C. and fused dimethyl oxalate was introduced at a rate of 56.3 mmol/h. The reaction was continued for 18 hours. At a lapse of 4 hours, a portion of the reaction mixture was taken out and subjected to gas chromatographic analysis.

Gas chromatographic analysis of the liquid reaction mixture taken out after 4 hrs. reaction indicated that a conversion ratio of dimethyl oxalate was 98.86, a selectivity to dimethyl carbonate was 85.1%, and a space time yield (STY) was 853 g/L·h. Gas chromatographic analysis of the liquid reaction mixture taken out after 18 hrs. reaction indicated that a conversion ratio of dimethyl oxalate was 99.0%, a selectivity to dimethyl carbonate was 88.7%, and a space time yield (STY) of dimethyl carbonate was 891 g/L·h.

EXAMPLE 4

Preparation of Catalyst/carrier Composition

The procedures of Example 1 were repeated except for replacing 1 g of potassium carbonate with 1 g of rubidium carbonate, to give a catalyst deposited on an active carbon. The rubidium carbonate was deposited on the active carbon at a ratio of 7.4 weight % in terms of the amount of rubidium.

Preparation of Dimethyl Carbonate

The procedures of Example 1 were repeated using 5 mL of the above-prepared catalyst/carrier composition except that the reaction temperature was changed to 220° C. and fused dimethyl oxalate was introduced at a rate of 57.6 mol/h. The reaction was continued for 6 hours.

Gas chromatographic analysis of the liquid reaction mixture indicated that a conversion ratio of dimethyl oxalate was 100%, a selectivity to dimethyl carbonate was 95.1%, and a space time yield (STY) of dimethyl carbonate was 987 g/L·h.

EXAMPLE 5

Preparation of Catalyst/carrier Composition

The procedures of Example 1 were repeated except for replacing 1 g of potassium carbonate with 1 g of cesium carbonate, to give a catalyst deposited on an active carbon. The cesium carbonate was deposited on the active carbon at a ratio of 8.2 weight % in terms of the amount of cesium.

Preparation of Dimethyl Carbonate

The procedures of Example 1 were repeated using 5 mL of the above-prepared catalyst/carrier composition except that the reaction temperature was changed to 220° C. and fused dimethyl oxalate was introduced at a rate of 57.4 mmol/h. The reaction was continued for 6 hours.

Gas chromatographic analysis of the liquid reaction mixture indicated that a conversion ratio of dimethyl oxalate was 100%, a selectivity to dimethyl carbonate was 94.6%, and a space time yield (STY) of dimethyl carbonate was 978 g/L·h.

EXAMPLE 6

Preparation of Catalyst/carrier Composition

The procedures of Example 1 were repeated except for replacing 1 g of potassium carbonate with 2 g of potassium hydroxide, to give a catalyst deposited on an active carbon. The potassium hydroxide was deposited on the active carbon at a ratio of 13.9 weight % in terms of the amount of potassium.

Preparation of Dimethyl Carbonate

The procedures of Example 1 were repeated using the above-prepared catalyst/carrier composition except that the reaction temperature was changed to 200° C. and fused dimethyl oxalate was introduced at a rate of 54.0 mmol/h.

Gas chromatographic analysis of the liquid reaction mixture obtained after 2 hrs. reaction indicated that a conversion ratio of dimethyl oxalate was 92.7%, a selectivity to dimethyl carbonate was 90.8%, and a space time yield (STY) of dimethyl carbonate was 819 g/L·h.

EXAMPLE 7

Preparation of Catalyst/carrier Composition

The procedures of Example 1 were repeated except for replacing 1 g of potassium carbonate with 1 g of potassium chloride, to give a catalyst deposited on an active carbon. The potassium chloride was deposited on the active carbon at a ratio of 5.2 weight % in terms of the amount of potassium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 66.8 mmol/h. The reaction was continued for 4 hours.

Gas chromatographic analysis of the liquid reaction mixture indicated that a conversion ratio of dimethyl oxalate was 100%, a selectivity to dimethyl carbonate was 95.0%, and a space time yield (STY) of dimethyl carbonate was 1,143 g/L·h.

EXAMPLE 8

Preparation of Catalyst/carrier Composition

The procedures of Example 1 were repeated except for replacing 1 g of potassium carbonate with 1 g of potassium bromide, to give a catalyst deposited on an active carbon. The potassium bromide was deposited on the active carbon at a ratio of 3.3 weight % in terms of the amount of potassium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 66.9 mmol/h.

Gas chromatographic analysis of the liquid reaction mixture obtained after 2 hrs. reaction indicated that a conversion ratio of dimethyl oxalate was 100%, a selectivity to dimethyl carbonate was 95.3%, and a space time yield (STY) of dimethyl carbonate was 1,149 g/L·h.

EXAMPLE 9

Preparation of Catalyst/carrier Composition

The procedures of Example 1 were repeated except for replacing 1 g of potassium carbonate with 1 g of potassium nitrate, to give a catalyst deposited on an active carbon. The potassium nitrate was deposited on the active carbon at a ratio of 3.9 weight % in terms of the amount of potassium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 66.5 mmol/h. The reaction was continued for 4 hours.

Gas chromatographic analysis of the liquid reaction mixture indicated that a conversion ratio of dimethyl oxalate was 100%, a selectivity to dimethyl carbonate was 94.7%, and a space time yield (STY) of dimethyl carbonate was 1,135 g/L·h.

The results of Examples 1 to 9 are set forth in Table 1.

TABLE 1

| Example No. | Catalyst | DMO (mmol) | Tem. (° C.) | Time (hr.) | DMO Con. (%) | DMC Sel. (%) | DMC STY (g/L · h) |
|---|---|---|---|---|---|---|---|
| Example 1 | $K_2CO_3$ | 66.7 | 205 | 2 | 100 | 95.0 | 1,142 |
| Example 2 | $Na_2CO_3$ | 55.6 | 250 | 4 | 87.2 | 75.1 | 656 |
| Example 3 | $NaKCO_3$ | 56.3 | 230 | 4 | 98.8 | 85.1 | 853 |
|  |  |  |  | 18 | 99.0 | 88.7 | 891 |
| Example 4 | $Rb_2CO_3$ | 57.6 | 220 | 6 | 100 | 95.1 | 987 |
| Example 5 | $Cs_2CO_3$ | 57.4 | 220 | 6 | 100 | 94.6 | 978 |
| Example 6 | KOH | 54.0 | 200 | 2 | 92.7 | 90.8 | 819 |
| Example 7 | KCl | 66.8 | 210 | 4 | 100 | 95.0 | 1,143 |
| Example 8 | KBr | 66.9 | 210 | 2 | 100 | 95.3 | 1,149 |
| Example 9 | $KNO_3$ | 66.5 | 210 | 4 | 100 | 94.7 | 1,135 |

Remarks:
DMO — dimethyl oxalate
DMC — dimethyl carbonate

EXAMPLE 10

Preparation of Catalyst/carrier Composition

The procedures of Example 1 were repeated except for replacing 1 g of potassium carbonate with 1 g of potassium acetate, to give a catalyst deposited on an active carbon. The potassium acetate was deposited on the active carbon at a ratio of 4.0 weight % in terms of the amount of potassium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 66.3 mmol/h.

Gas chromatographic analysis of the liquid reaction mixture obtained after 2 hrs. reaction indicated that a conversion ratio of dimethyl oxalate was 100%, a selectivity to dimethyl carbonate was 95.1%, and a space time yield (STY) of dimethyl carbonate was 1,136 g/L·h.

EXAMPLE 11

Preparation of Catalyst/carrier Composition

The procedures of Example 1 were repeated except for replacing 1 g of potassium carbonate with 1 g of potassium oxalate, to give a catalyst deposited on an active carbon. The potassium oxalate was deposited on the active carbon at a ratio of 4.7 weight % in terms of the amount of potassium.

Preparation of Dimethyl Carbonate

The procedures of Example 1 were repeated using 5 mL of the above-prepared catalyst/carrier composition except that the reaction temperature was changed to 200° C. and fused dimethyl oxalate was introduced at a rate of 32.5 mmol/h.

Gas chromatographic analysis of the liquid reaction mixture obtained after 2 hrs. reaction indicated that a conversion ratio of dimethyl oxalate was 100%, a selectivity to dimethyl carbonate was 95.4%, and a space time yield (STY) of dimethyl carbonate was 559 g/L·h.

EXAMPLE 12

Preparation of Dimethyl Carbonate

The procedures of Example 1 were repeated using 5 mL of the catalyst/carrier composition obtained in Example 11 except that the reaction temperature was changed to 200° C. and fused dimethyl oxalate was introduced at a rate of 58.3 mmol/h.

Gas chromatographic analysis of the liquid reaction mixture obtained after 2 hrs. reaction indicated that a conversion ratio of dimethyl oxalate was 100%, a selectivity to dimethyl carbonate was 96.3%, and a space time yield (STY) of dimethyl carbonate was 1,011 g/L·h.

EXAMPLE 13

Preparation of Dimethyl Carbonate

The procedures of Example 1 were repeated using 5 mL of the catalyst/carrier composition obtained in Example 11 except that the reaction temperature was changed to 210° C. and fused dimethyl oxalate was introduced at a rate of 122.6 mmol/h.

Gas chromatographic analysis of the liquid reaction mixture obtained after 2 hrs. reaction indicated that a conversion ratio of dimethyl oxalate was 93.9%, a selectivity to dimethyl carbonate was 96.9%, and a space time yield (STY) of dimethyl carbonate was 2,010 g/L·h.

EXAMPLE 14

Preparation of Dimethyl Carbonate

The procedures of Example 1 were repeated using 5 mL of the catalyst/carrier composition obtained in Example 11 except that the reaction temperature was changed to 220° C. and fused dimethyl oxalate was introduced at a rate of 180.8 mmol/h.

Gas chromatographic analysis of the liquid reaction mixture obtained after 2 hrs. reaction indicated that a conversion ratio of dimethyl oxalate was 100%, a selectivity to dimethyl carbonate was 96.1%, and a space time yield (STY) of dimethyl carbonate was 3,130 g/L·h.

EXAMPLE 15

Preparation of Dimethyl Carbonate

The procedures of Example 1 were repeated using 5 mL of the catalyst/carrier composition obtained in Example 11 except that the reaction temperature was changed to 230° C. and fused dimethyl oxalate was introduced at a rate of 279.3 mmol/h.

Gas chromatographic analysis of the liquid reaction mixture obtained after 2 hrs. reaction indicated that a conversion ratio of dimethyl oxalate was 90.3%, a selectivity to dimethyl carbonate was 95.0, and a space time yield (STY) of dimethyl carbonate was 4,317 g/L·h.

EXAMPLE 16

Preparation of Catalyst/carrier Composition

The procedures of Example 1 were repeated except for replacing 1 g of potassium carbonate with 1 g of rubidium oxalate, to give a catalyst deposited on an active carbon. The rubidium oxalate was deposited on the active carbon at a ratio of 6.6 weight % in terms of the amount of rubidium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 56.4 mmol/h.

Gas chromatographic analysis of the liquid reaction mixture obtained after 2 hrs. reaction indicated that a conversion ratio of dimethyl oxalate was 100%, a selectivity to dimethyl carbonate was 95.9%, and a space time yield (STY) of dimethyl carbonate was 974 g/L·h.

EXAMPLE 17

Preparation of Catalyst/carrier Composition

The procedures of Example 1 were repeated except for replacing 1 g of potassium carbonate with 1 g of cesium oxalate, to give a catalyst deposited on an active carbon. The cesium oxalate was deposited on the active carbon at a ratio of 7.5 weight % in terms of the amount of cesium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 56.4 mmol/h. The reaction was continued for 6 hours.

Gas chromatographic analysis of the liquid reaction mixture indicated that a conversion ratio of dimethyl oxalate was 100%, a selectivity to dimethyl carbonate was 95.2%, and a space time yield (STY) of dimethyl carbonate was 967 g/L·h.

EXAMPLE 18

Preparation of Catalyst/carrier Composition

The procedures of Example 1 were repeated except for replacing 1 g of potassium carbonate with 1 g of potassium phosphate, to give a catalyst deposited on an active carbon. The potassium phosphate was deposited on the active carbon at a ratio of 5.5 weight % in terms of the amount of potassium.

Preparation of Dimethyl Carbonate

The procedures of Example 1 were repeated using 5 mL of the above-prepared catalyst/carrier composition except that the reaction temperature was changed to 210° C. and fused dimethyl oxalate was introduced at a rate of 66.7 mmol/h. The reaction was continued for 3 hours.

Gas chromatographic analysis of the liquid reaction mixture indicated that a conversion ratio of dimethyl oxalate was 100%, a selectivity to dimethyl carbonate was 95.2%, and a space time yield (STY) of dimethyl carbonate was 1,140 g/L·h.

The results of Examples 10 to 18 are set forth in Table 2.

TABLE 2

| Example No. | Catalyst | DMO (mmol) | Tem. (° C.) | Time (hr.) | DMO Con. (%) | DMC Sel. (%) | DMC STY (g/L·h) |
|---|---|---|---|---|---|---|---|
| Example 10 | KOCOCH$_3$ | 66.3 | 210 | 2 | 100 | 95.1 | 1,142 |
| Example 11 | K$_2$C$_2$O$_4$ | 32.5 | 200 | 2 | 100 | 95.4 | 559 |
| Example 12 | K$_2$C$_2$O$_4$ | 58.3 | 200 | 2 | 100 | 96.3 | 1,011 |
| Example 13 | K$_2$C$_2$O$_4$ | 122.6 | 210 | 2 | 93.9 | 96.9 | 2,010 |
| Example 14 | K$_2$C$_2$O$_4$ | 180.8 | 220 | 2 | 100 | 96.1 | 3,130 |
| Example 15 | K$_2$C$_2$O$_4$ | 279.3 | 230 | 2 | 90.3 | 95.0 | 4,317 |
| Example 16 | Rb$_2$C$_2$O$_4$ | 56.4 | 210 | 2 | 100 | 95.9 | 974 |
| Example 17 | Cs$_2$C$_2$O$_4$ | 56.4 | 210 | 6 | 100 | 95.2 | 967 |
| Example 18 | K$_3$PO$_4$ | 66.7 | 210 | 3 | 100 | 95.2 | 1,140 |

Remarks:
DMO — dimethyl oxalate
DMC — dimethyl carbonate

EXAMPLE 19

Preparation of Catalyst Composition

Potassium carbonate was molded in a pressure molding machine to give a catalyst composition having a granular size of approximately 3 mm.

Preparation of Dimethyl Carbonate

The procedures of Example 1 were repeated using 10 mL of the above-prepared catalyst composition except that the reaction temperature was changed to 220° C. and fused dimethyl oxalate was introduced at a rate of 125.5 mmol/h.

Gas chromatographic analysis of the liquid reaction mixture obtained after 2 hrs. reaction indicated that a conversion ratio of dimethyl oxalate was 82.3%, a selectivity to dimethyl carbonate was 81.5%, and a space time yield (STY) of dimethyl carbonate was 758 g/L·h.

EXAMPLE 20

Preparation of Catalyst Composition

Potassium oxalate was molded in a pressure molding machine to give a catalyst composition having a granular size of approximately 3 mm.

Preparation of Dimethyl Carbonate

The procedures of Example 1 were repeated using 10 mL of the above-prepared catalyst composition except that the reaction temperature was changed to 230° C. and fused dimethyl oxalate was introduced at a rate of 56.4 mmol/h.

Gas chromatographic analysis of the liquid reaction mixture obtained after 2 hrs. reaction indicated that a conversion ratio of dimethyl oxalate was 83.6%, a selectivity to dimethyl carbonate was 98.1%, and a space time yield (STY) of dimethyl carbonate was 417 g/L·h.

EXAMPLE 21

Preparation of Dimethyl Carbonate

The procedures of Example 1 were repeated using 10 mL of the catalyst composition prepared in Example 20 except that the reaction temperature was changed to 250° C. and fused dimethyl oxalate was introduced at a rate of 56.4 mmol/h.

Gas chromatographic analysis of the liquid reaction mixture obtained after 2 hrs. reaction indicated that a conversion ratio of dimethyl oxalate was 98.26, a selectivity to dimethyl carbonate was 97.7%, and a space time yield (STY) of dimethyl carbonate was 487 g/L·h.

EXAMPLE 22

Preparation of Dimethyl Carbonate

The procedures of Example 1 were repeated using 10 mL of the catalyst composition prepared in Example 20 except that the reaction temperature was changed to 280° C. and fused dimethyl oxalate was introduced at a rate of 56.4 mmol/h.

Gas chromatographic analysis of the liquid reaction mixture obtained after 2 hrs. reaction indicated that a conversion ratio of dimethyl oxalate was 100%, a selectivity to dimethyl carbonate was 97.8%, and a space time yield (STY) of dimethyl carbonate was 497 g/L·h.

EXAMPLE 23

Preparation of Catalyst Composition

Rubidium oxalate was molded in a pressure molding machine to give a catalyst composition having a granular size of approximately 3 mm.

Preparation of Dimethyl Carbonate

The procedures of Example 1 were repeated using 5 mL of the above-prepared catalyst composition except that the reaction temperature was changed to 250° C. and fused dimethyl oxalate was introduced at a rate of 56.4 mmol/h. The reaction was continued for 4 hours.

Gas chromatographic analysis of the liquid reaction mixture indicated that a conversion ratio of dimethyl oxalate was 64.4%, a selectivity to dimethyl carbonate was 97.3%, and a space time yield (STY) of dimethyl carbonate was 637 g/L·h.

The results of Examples 19 to 23 are set forth in Table 3.

TABLE 3

| Example No. | Catalyst | DMO (mmol) | Tem. (° C.) | Time (hr.) | DMO Con. (%) | DMC Sel. (%) | DMC STY (g/L·h) |
| --- | --- | --- | --- | --- | --- | --- | --- |
| Example 19 | $K_2CO_3$ | 125.5 | 220 | 2 | 82.3 | 81.5 | 758 |
| Example 20 | $K_2C_2O_4$ | 56.4 | 230 | 2 | 83.6 | 98.1 | 417 |
| Example 21 | $K_2C_2O_4$ | 56.4 | 250 | 2 | 98.2 | 97.7 | 487 |
| Example 22 | $K_2C_2O_4$ | 56.4 | 280 | 2 | 100 | 97.8 | 497 |
| Example 23 | $Rb_2C_2O_4$ | 56.4 | 250 | 4 | 64.4 | 97.3 | 637 |

Remarks:
DMO — dimethyl oxalate
DMC — dimethyl carbonate

What is claimed is:

1. A process for preparing a dialkyl carbonate which comprises decarbonylation of a dialkyl oxalate in a gaseous phase in the presence of an alkali metal compound.

2. The process of claim 1, wherein the alkali metal compound is an organic acid salt of an alkali metal, an inorganic acid salt of an alkali metal, a hydroxide of an alkali metal, or an oxide of an alkali metal.

3. The process of claim 1, wherein the alkali metal compound is a carbonate of potassium, sodium, sodium potassium, rubidium or cesium.

4. The process of claim 1, wherein the alkali metal compound is a halide of potassium, sodium, rubidium or cesium.

5. The process of claim 1, wherein the alkali metal compound is a nitrate of potassium, sodium, rubidum, or cesium.

6. The process of claim 1, wherein the alkali metal compound is an aliphatic monocarboxylate of potassium, sodium, rubidium or cesium.

7. The process of claim 1, wherein the alkali metal compound is an oxalate of potassium, sodium, rubidium or cesium.

8. The process of claim 1, wherein the alkali metal compound is a phosphate of potassium, sodium, rubidium or cesium.

9. The process of claim 1, wherein the dialkyl carbonate and the dialkyl oxalate are a carbonate of two alkyl groups and an oxalate of two alkyl groups, each of which independently is an alkyl group having 1 to 4 carbon atoms.

10. The process of claim 1, wherein the dialkyl carbonate is dimethyl carbonate and the dialkyl oxalate is dimethyl oxalate.

11. The process of claim 1, wherein the alkali metal compound is deposited on a carrier in an amount of 0.01 to 80 weight percent in terms of the amount of alkali metal.

12. The process of claim 1, wherein the decarbonylation is performed at a temperature in the range of 170 to 450° C.

13. The process of claim 1, wherein the decarbonylation is continuously performed in a reaction vessel into which a gaseous composition comprising the dialkyl oxalate is supplied at a space velocity of 100 to 5,000 $h^{-1}$.

* * * * *